United States Patent [19]

Brackeen et al.

[11] Patent Number: 5,006,657

[45] Date of Patent: Apr. 9, 1991

[54] INTERMEDIATES IN A RESOLUTION PROCESS FOR RACEMIC SPIRO HYDANTOINS

[75] Inventors: Marcus Brackeen, Durham, N.C.; Harry R. Howard, Jr., Hartford, Conn.

[73] Assignee: Pfizer Inc., New York, N.Y.

[21] Appl. No.: 543,986

[22] Filed: Jun. 25, 1990

Related U.S. Application Data

[62] Division of Ser. No. 224,966, Jul. 27, 1988, Pat. No. 4,952,694.

[51] Int. Cl.$^5$ .................. C07D 215/38; C07D 491/10
[52] U.S. Cl. ........................................ 546/18; 546/15; 548/308; 548/309
[58] Field of Search ................... 548/308, 309; 546/15, 546/18

[56] References Cited

U.S. PATENT DOCUMENTS

| | | | |
|---|---|---|---|
| 4,117,230 | 9/1978 | Sarges | 548/309 |
| 4,130,714 | 12/1978 | Sarges | 548/309 |
| 4,716,113 | 12/1987 | Urban | 435/125 |

FOREIGN PATENT DOCUMENTS

| | | | |
|---|---|---|---|
| 0553839 | 5/1986 | Australia | 548/308 |
| 0109231 | 5/1984 | European Pat. Off. | 548/308 |
| 8602647 | 5/1986 | PCT Int'l Appl. | 548/308 |

OTHER PUBLICATIONS

Reinhard Sarges et al., in the *Journal of Organic Chemistry*, vol. 47, p. 4081 (1982).
William H. Pirkle et al., in the *Journal of Organic Chemistry*, vol. 49, p. 2433 (1984).

*Primary Examiner*—Richard L. Raymond
*Assistant Examiner*—Mark W. Russell
*Attorney, Agent, or Firm*—Peter C. Richardson; Paul H. Ginsburg

[57] ABSTRACT

A novel three-step process for resolving a racemic spiro-hydantoin compound into its optical antipodes is disclosed, which involves (1) reacting said racemic compound with an optically-active asymmetric isocyanate of the formula RNCO, wherein R is (S)- or (R)-1-phenylethyl or (S)-or (R)-1-(1-naphthyl)ethyl, to form the corresponding diastereomeric ureido compound; (2) separating the resulting diastereomeric mixture into its component parts, and (3) thereafter converting the separated ureido diasteromers obtained in step (b) to the corresponding asymmetric hydantoin compounds by treatment with an alkali metal lower alkoxide ($C_1$–$C_4$), followed by acidification, whereupon the desired optical isomer is obtained. The final products so obtained, such as (4S)-(+)-6-fluoro-2,3-dihydro-spiro-[4H-1-benzopyran-4,4'-imidazolidine]-2',5'-dione(sorbinil) and (5'S)-3'-chloro-5', 6',7',8'-tetrahydro-spiro[imidazolidine-4,5'-quinoline]-2,5-dione, are known to be useful in preventing or alleviating certain chronic diabetic complications. The aforementioned diastereomeric ureido intermediates are novel compounds.

5 Claims, No Drawings

INTERMEDIATES IN A RESOLUTION PROCESS FOR RACEMIC SPIRO HYDANTOINS

This is a division of application Ser. No. 224,966, filed on July 27, 1988, now U.S. Pat. No. 4,952,694.

BACKGROUND OF THE INVENTION

This invention relates to a new and useful process for resolving a racemic spiro-hydantoin compound into its optical antipodes. More particularly, it is concerned with a novel three-step process for preparing various optically-active asymmetric spiro-hydantoin compounds (including sorbinil), which are known to be of value in the medical control of certain chronic diabetic complications arising from diabetes mellitus. The invention also includes within its scope certain corresponding novel ureido compounds, which are used as intermediates in the aforesaid novel process.

In accordance with the prior art, it is now known that certain optical isomers of various asymmetric spiro-hydantoin compounds are useful as aldose reductase inhibitors and hence, of value in the treatment of certain chronic diabetic complications such as diabetic cataracts, neuropathy and retinopathy, etc. Included among these agents are such optically-active compounds as (4S)-(+)-6-fluoro-2,3-dihydro-spiro[4H-benzopyran-4,4'-imidazolidine]-2',5'-dione (sorbinil), which is described and claimed by R. Sarges in U.S. Pat. No. 4,130,714 and (5'S)-3'-chloro-5',6',7',8'-tetrahydro-spiro[imidazolidine-4,5'-quinoline]-2,5-dione which is disclosed by C. A. Lipinski in Published European Patent Application No. 180,421 (published May 7, 1986).

In the past, these particular compounds (i.e., optical isomers) have been obtained by various means. For instance, sorbinil was first obtained after resolution of the corresponding dl-compound with 1-brucine and reported as d-6-fluoro-spiro[chroman-4,4'-imidazolidine]-2',5'-dione by R. Sarges in aforesaid U.S. Pat. No 4,130,714. Later synthetic developments involved the use of asymmetric induction starting with a ketone precursor (viz., 6-fluoro-2,3-dihydro-4H-1-benzopyran-4-one) and optically-active (S)-α-methylbenzylamine in the presence of titanium tetrachloride, as reported by R. Sarges et al. in the *Journal of Chemical Society*, Vol. 47, p. 4081 (1982); while more recently, in U.S. Pat. No. 4,716,113 to F. J. Urban, there is described a multi-step process for preparing sorbinil, starting from 2-(4'-fluorophenoxy)ethyl bromide, wherein the enzyme α-chymotrypsin is employed to resolve the intermediate known as methyl 4-amino-6-fluorochroman-4-carboxylate into its respective optical antipodes prior to conversion to the desired spiro-hydantoin ring compound via treatment with an alkali metal cyanate in an acid medium.

In the search for improved methods of production in this particular area, little is known about the use of other methods of asymmetric induction, such as the reaction of an asymmetric isocyanate with the spiro-hydantoin ring system, etc., even though these methods have been briefly employed in the pas with variable success in the field of heterocyclic chemistry when applied to other heterocyclic ring systems. For instance, in a paper by W. H. Pirkle et al., appearing in the *Journal of Organic Chemistry*, Vol. 49, p. 2433 (1984), there is described a method for resolving several chiral lactams by reacting said compounds with a chiral isocyanate, such as α-phenylethyl isocyanate, to afford the corresponding diastereomeric ureides that are then readily separable by means of chromatography on silica; the desired lactam enantiomers are thereafter retrieved from the separated ureides by means of hydrolysis.

SUMMARY OF THE INVENTION

In accordance with the present invention, there is now provided a new and improved process for resolving a racemic spiro-hydantoin compound of the type previously discussed into its optical antipodes by a novel three-step method which involves the steps of
(a) reacting a racemic compound of the formula:

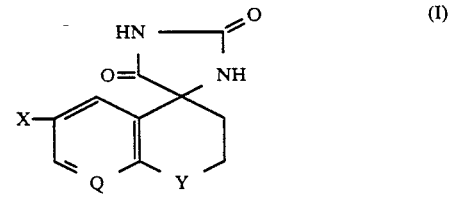

wherein X is hydrogen, fluorine, chlorine, bromine, $C_1$-$C_4$ alkyl or $C_1$-$C_4$ alkoxy, Q is methine or nitrogen and Y is methylene, oxygen or sulfur, in a reaction-inert polar organic solvent with at least an equimolar amount of an optically-active asymmetric isocyanate of the formula RNCO, wherein R is, for example, (S)- or (R)-1-phenylethyl or (S)- or (R)-1-(1-naphthyl)ethyl, in the presence of a base at a temperature that is in the range of from about 5° C. up to about 40° C. until the reaction to form the diastereomeric ureido compound of the formula:

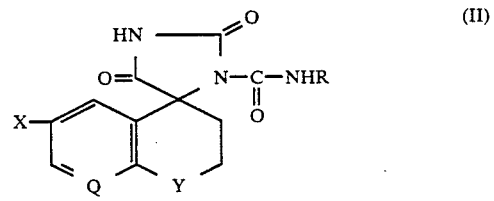

wherein X, Q, Y and R are each as previously defined, is substantially complete;

(b) separating the resulting diastereomeric mixture into its component parts; and (c) thereafter converting the separated ureido diastereomers obtained in step (b) to the corresponding asymmetric hydantoin compounds by treatment with an excess in moles of an alkali metal lower alkoxide ($C_1$-$C_4$) in an aprotic organic solvent at a temperature that is in the range of from 20° C. to the reflux temperature of the reaction mixture, followed by acidification whereupon the desired optical isomer is obtained in pure form and in high yield.

In this way, a compound such as racemic 6-fluoro-2,3-dihydro-spiro[4H-1-benzopyran-4,4'-imidazolidine]-2',5'-dione is readily converted, via the novel intermediate (4S)-6-fluoro-2,3-dihydro-3'-[(R)-1-phenylethylcarbamoyl]spiro[4H-1-benzopyran-4,4'-imidazolidine]-2',5'-dione, to (4S)-(+)-6-fluoro-2,3-dihydro-spiro[4H-1-benzopyran-4,4'-imidazolidine]-2',5'-dione (sorbinil) in a most facile manner without the disadvantages connected with the prior art techniques. In like manner, racemic 3'-chloro-5',6',7',8'-tetrahydro-spiro[imidazolidine-45'-quinoline]-2,5-dione is converted, via the novel intermediate (5'S)-3'-chloro-5',6',7',8'-tetrahydro-3-[(R)-1-phenylethylcarbamoyl]spiro[imidazolidine-4,5'- quinoline]-2,5-dione, to (5'S)-3'-chloro-5',6',7',8'-tetrahydro-spiro[imidazolidine-4,5'-quinoline]-2,5-dione in an equally facile way.

Accordingly, there is also included within the purview of this invention the novel intermediates used in the process, such as the diastereomeric ureido compounds produced in step (a), which are useful as intermediates leading to the separated diastereomers produced in step (b) that ultimately afford the desired optically-active spiro-hydantoin final products previously described. The present invention therefore includes a novel diastereomeric ureide compound of the formula:

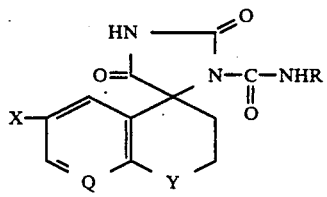

(II)

wherein X is hydrogen, fluorine, chlorine, bromine, $C_1$–$C_4$ alkyl or $C_1$–$C_4$ alkoxy; Q is methine or nitrogen; Y is methylene, oxygen or sulfur; and R is (S)- or (R)-1-phenylethyl or 1-(1-naphthyl)ethyl. Preferred compounds within this category include those of the above formula wherein X is fluorine, Q is methine and Y is oxygen, as well as those wherein X is chlorine, Q is nitrogen and Y is methylene. R is most preferably (R)-1-phenylethyl in either instance. Particularly preferred compounds for these purposes include (4S)-6-fluoro-2,3-dihydro-3'-[(R)-1-phenylethylcarbamoyl]spiro[4H-1-benzopyran-4,4'-imidazolidine]-2',5'-dione and (5'S)-3'-chloro-5',6',7',8'-tetrahydro-3-[(R)-1-phenylethylcarbamoyl]spiro[imidazolidine-4,5'-quinoline]-2,5-dione, as these are the intermediates that specifically lead to sorbinol and (5'S)-3'-chloro-5',6',7',8'-tetrahydro-spiro[imidazolidine-4,5'-quinoline]-2,5-dione, respectively, as previously discussed.

DETAILED DESCRIPTION OF THE INVENTION

In accordance with the process of this invention, the reaction of a racemic spiro-hydantoin compound of structural formula (I), wherein X, Q and Y are each as previously defined, with an optically-active asymmetric isocyanate of the formula RNCO, where R is also as previously defined, to form the corresponding diastereomeric ureido compound of structural formula (II), as set forth in step (a), is most effectively carried out by conducting said reaction in a basic solvent medium. More particularly, this is best accomplished by conducting the reaction in a reaction-inert polar organic solvent such as a cyclic ether like dioxane or tetrahydrofuran, or a lower dialkyl ($C_1$–$C_3$) sulfoxide or a lower N,N-dialkyl lower alkanoamide having up to a total of five carbon atoms and by preferably using at least an equimolar amount of base such as an organic tertiary-amine like triethylamine or pyridine or an alkali metal hydride like lithium or sodium hydride (in mineral oil), etc., with respect to the racemic spiro-hydantoin starting material. Preferred lower dialkyl sulfoxides for use as solvents in this connection include dimethyl sulfoxide, diethyl sulfoxide and di-n-propyl sulfoxide, while preferred lower N,N-dialkyl lower alkanoamides include dimethylformamide, diethylformamide and dimethylacetamide. The optically-active isocyanate compounds (RNCO) employed as reagents in this reaction are all known compounds and are readily available commercially or else easily prepared by those skilled in the art, using well-known methods that start from readily available materials. It is usually preferable to employ at least about a molar equivalent of the isocyanate reagent in the aforesaid reaction of step (a) of the present invention and in many instances, it is even most desirable to employ substantially equimolar amounts of racemic compound and optically-active asymmetric isocyanate in order to effectively minimize the cost and to maximize the purity of product. In general, the reaction is conducted at a temperature that is in the range of from about 5° C. up to about 40° C. until the reaction to form the diastereomeric ureido compound is substantially complete. This, in turn, will often preferably require a period of at least about 18 hours when the reaction is most conveniently conducted at room temperature. Upon completion of this reaction step, the desired diastereomeric ureido compound (which is a mixture of diastereomeric ureides) is easily recovered from the reaction mixture by any number of conventional techniques and most preferably by first diluting same with ice/water and then extracting with a water-immiscible organic solvent such as diethyl ether, or else by acidifying the chilled aqueous mixture so as to precipitate the desired product therefrom.

The diastereomeric mixture of ureides formed in step (a) is then separated into its component parts by such means as fractional crystallization, column chromatography and the like, and most preferably by means of chromatography on silica in accordance with the standard techniques of analytical organic chemistry. For instance, the diastereomers formed by reacting racemic 6-fluoro-2,3-dihydro-spiro[4H-1-benzopyran-4,4'-imidazolidine]-2',5'-dione of U.S. Pat. No. 4,130,714 with either (R)-(+)- or (S)-(-)-α-methylbenzyl isocyanate or with (R)-(-)- or (S)-(+)-(α-naphthyl)ethyl isocyanate are all separated chromatographically via column chromatography on silica gel, as is more fully described in the experimental section of the instant specification (see Example 1–4 in this regard). In like manner, the diastereomers formed by reacting racemic 3'-chloro-5',6',7',8'-tetrahydro-spiro[imidazolidine-4,5'-quinoline]-2,5-dione (generically disclosed in European Patent Application No. 180,421, published May 7, 1986) with either (R)-(+)- or (S)-(-)-αmethylbenzyl isocyanate or with (R)-(-)- or (S)-(+)-α-(naphthyl)ethyl isocyanate are also each similarly resolved by means of column chromatography on silica gel.

The third and final stage of the three-step process of the present invention involves converting the separated ureido diastereomers obtained in step (b) to the corresponding optically-active hydantoin compounds by treatment with an excess in moles of a an alkali metal lower alkoxide ($C_{1-4}$), such as sodium methoxide, sodium ethoxide, lithium methoxide and potassium tert.-butoxide, in an aprotic organic solvent at a temperature that is in the range of from about 20° C. up to the reflux temperature of the reaction mixture, followed by acidification, whereupon the desired optical isomer is obtained. Preferred aprotic organic solvents include acetonitrile, cyclic ethers such as dioxane and tetrahydrofuran, as well as lower N,N-dialkyl lower alkanoamides having up to a total of five carbon atoms such as dimethylformamide, diethylformamide and dimethylacetamide. The preferred alkali metal alkoxide reagent for the hydrolysis reaction of step (c) is sodium methoxide, while the preferred solvent is tetrahydrofuran. In a preferred embodiment of this particular step, the molar ratio of the alkali metal alkoxide to separated ureido diastereomer is from about 3:1 to about 30:1, respectively, while the preferred temperature range is from about 65° C. to about 100° C. when the reaction is conducted for a period that is preferably from about four to about 48 hours. Upon completion of this step, the desired optically-active hydantoin compound is then recovered from the reaction mixture as a non-salt by first concentrating said mixture under reduced pressure, then diluting same with water (if necessary) and thereafter adding a sufficient amount of dilute aqueous acid to cause precipitation of the desired spiro-hydantoin enantiomer therefrom.

The racemic spiro-hydantoin compounds required as starting materials (or as substrates) for conducting the resolution process of this invention are known compounds, which are readily prepared by those skilled in the art using classical methods of organic synthesis, starting from common chemical reagents and/or commercially available materials. For instance, racemic 6-fluoro-2,3-dihydro-spiro[4H-1-benzopyran-4,4'-imidazolidine]-2',5'-dione is readily prepared by employing the method of R. Sarges, as described in U.S. Pat. No. 4,130,714 where it was first reported as dl-6-fluoro-spiro-[chroman-4,4'-imidazolidine]-2',5'-dione, while racemic 3'-chloro-5',6',7',8'-tetrahydrospiro[imidazolidine-4,5'-quinoline]-2,5-dione is more easily prepared by employing the general methods set forth by R. Sarges in U.S. Pat. No. 4,117,230 and by C. A. Lipinski in Published European Patent Application No. 180,421 (published May 7, 1986), as is more specifically described in detail in the experimental section of the instant specification (see Preparations A thru E in this regard). The other racemic spiro-hydantoin starting materials of this invention can also be prepared by using the specific synthetic methods of U.S. Pat. Nos. 4,117,230 and 4,130,714 or else by employing the general methods of the aforementioned published European patent application as previously discussed.

As previously indicated, the optically-active spiro-hydantoin final product afforded by the proces of this invention, such as (4S)-(+)-6-fluoro-2,3-dihydro-spiro[4H-1-benzopyran-4,4'-imidazolidine]-2',5'-dione (sorbinil) and (5'S)-3'-chloro-5',6',7',8'-tetrahydro-spiro[imidazolidine-4,5'-quinoline]-2,5-dione and the like, are known to be useful in the field of medicinal chemistry for preventing or alleviating certain chronic diabetic complications caused by diabetes mellitus (see U.S. Pat. Nos. 4,117,230, 4,130,714 and Published European Patent Application No. 180,421 for example).

Hence, the novel process of the present invention now provides the required and valuable optically-active spiro-hydantoin enantiomers discussed above in pure form and in high yield by a unique three-step method, which represents a major improvement over prior art methods in view of the ease of synthesis and the greatly reduced costs involved.

PREPARATION A

A mixture consisting of 250 g. (1.39 mole) of 1,1,2,3-tetrachloro-2-propene (Columbia Organic Chemical Co. of Camden, S.C.) and 250 ml. of 98% sulfuric acid was stirred at 36°–39° C. for a period of 16 hours. Upon completion of this step, the resulting solution was cooled to 25° C. and then poured slowly over 250 ml. of well-stirred ice/water contained in a large beaker that was cooled externally via a dry ice/acetone bath so as to always maintain the internal temperature of the stirred mixture well below 10° C. After further cooling the stirred mixture to below −40° C., the resulting solids were filtered and thereafter dried to constant weight to ultimately afford 105.2 g. (71%) of crude 2-chloromalonaldehyde.

PREPARATION B

A solution consisting of 105.2 g. (1.0 mole) of 2-chloromalonaldehyde (the product of Preparation A) dissolved in 500 ml. of methylene chloride was treated with 72 ml. (1.0 mole) of thionyl chloride and then heated to a gentle reflux until it became homogeneous once again. At this point, further heating was discontinued and the solvent and excess thionyl chloride were then removed from the reaction mixture by means of evaporation under reduced pressure (using a rotary evaporator without external heating). The viscous oily residue was substantially pure 1,2-dichloro-1-propen-3-al and was used as such in the next reaction step without any further purification being necessary.

PREPARATION C

In a three-liter reaction flask equipped with a Dean-Stark trap, there were placed 900 ml. of benzene under a dry nitrogen atmosphere. After heating the latter solvent to 70° C., 100 g. (0.89 mole) of 1,3-cyclohexanedione were added and the resulting solution was then treated with ammonia gas for a period of 1.75 hours. At this point, 14 ml. of water had collected in the trap (this was water of condensation from the reaction). The resulting reaction mixture was then allowed to cool down to 25° C. by standing overnight (ca. 16 hours), and the yellow solid material which formed was subsequently collected by means of suction filtration to ultimately afford 102.9 g. of crude 3-amino-2-cyclohexen-1-one. The yield of crude product was nearly quantitative. The latter material was used as such in the next reaction step without any further purification being necessary.

PREPARATION D

To a mechanically-stirred slurry consisting of 60 g. of lithium chloride in 350 ml. of anhydrous dimethylformamide at 40° C., there were added 88.9 g. (0.80 mole) of 3-amino-2-cyclohexene-1-one (the product of Preparation C). When all this material had dissolved, the temperature was increased to 60° C. and all of the 1,2-dichloro-1-propen-3-al obtained in Preparation B (i.e., the product of Preparation B) was added in one portion. This resulted in a mild exotherm accompanied by vigorous bubbling. After allowing the reaction mixture to stand at 90° C. for a period of one hour, the reaction flask and its contents were cooled to 25° C. and the contents were poured over 400 ml. of water. The resulting slurry was then extracted with twelve-500 ml. portions of hexanes, which were subsequently combined and then dried over anhydrous magnesium sulfate. After removal of the drying agent by means of filtration and the solvent by means of evaporation under reduced pressure, there were eventually obtained 51.62 g. (28%) of pure 3-chloro-5,6,7,8-tetrahydro-5-quinolone in the form of a yellow solid melting at 88°–94° C.; $^1$HNMR (300 MHz, DMSO-d$_6$)δ2.10 (m, 2H), 2.65 (t, 2H), 3.05 (t, 2H), 8.08 (s, 1H), 8.70 (s, 1H). The 28% yield of final product was based on the amount of 2- chloromalonaldehyde used as starting material in Preparation B.

PREPARATION E

A mixture consisting 51.62 g. (0.284 mole) of 3-chloro-5,6,7,8-tetrahydro-5-quinolone (the product of Preparation D), 32.22 g. (0.495 mole) of potassium cyanide, 167 g. (1.74 mole) of ammonium carbonate and 38.7 g. (0.372 mole) of sodium bisulfite in 400 ml. of formamide was placed in a stainless-steel autoclave that was equipped with mechanical stirrer and heated at 75° C. for a period of twelve hours (an internal pressure of ca. 200 p.s.i.g. developed). Upon completion of this step, the reaction mixture was cooled to 25° C. and the cooled contents of the autoclave were then removed and subsequently acidified to pH 7.0 with 6N hydrochloric acid, followed by further cooling to 0° C. to precipitate the crude product (yield, 61.71 g.). Recrystallization of the latter material from aqueous ethanol then gave, after drying in vacuo at 100° C./15 mm. Hg for 24 hours, 52.17 g. (73%) of pure racemic 3'-chloro-5',6',7',8'-tetrahydro-spiro[imidazolidine-4,5'-quinoline]-2,5-dione, m.p. 230°–233° C.; $^1$HNMR (300 MHz, DMSO-$d_6$)$\delta$1.82–2.02 (m, 2H), 2.05–2.30 (m, 2H), 2.88 (t, 2H), 7.63 (d, J=3Hz, 1H), 8.50 (d, J=3Hz, 1H), 8.57 (s, 1H).

EXAMPLE 1

Under an atmosphere of nitrogen in a flame-dried reaction flask, 271 mg. (0.00679 mole) of 60% sodium hydride (dispersed in mineral oil) was washed with hexane to remove the oil and thereafter was suspended in 15 ml. of dry dimethylformamide with constant agitation. To the resulting stirred suspension, there were then added in one portion 1.61 g. (0.00679 mole) of racemic 6-fluoro-2,3-dihydro-spiro-[4H-1-benzopyran-4,4'-imidazolidine]-2',5'-dione (prepared according to the procedure described by R. Sarges in U.S. Pat. No. 4,130,714), followed by an additional 5 ml. of dry dimethylformamide to facilitate stirring. After stirring the resulting slurry at room temperature (ca. 20° C.) for a period of 35 minutes, it was subsequently treated with 1.0 g. (0.00679 mole) of (R)-(+)-α-methylbenzyl isocyanate (Aldrich Chemical Company, Inc. of Milwaukee, Wisc.) and then stirred at room temperature for a period of 72 hours. Upon completion of this step; the reaction mixture was cooled to 0° C. and poured over 100 ml. of ice/water, followed by extraction of the aqueous mixture with three-50 ml. portions of diethyl ether. The combined organic layers were then dried over anhydrous magnesium sulfate and filtered, and the resulting filtrate subsequently concentrated in vacuo to afford 1.52 g. (58%) of crude product, which proved to be a mixture of diastereomeric ureides consisting of (4R)- and (4S)-6-fluoro-2,3-dihydro-3'-[(R)-1-phenylethylcarbamoyl]-spiro[4H-1-benzopyran-4,4'-imidazolidine]-2',5'-dione. The latter diastereomeric mixture was then chromatographed on silica gel (230–400 mesh), using hexane/ethyl acetate (7:3 by volume) as the eluant. In this way, there were ultimately obtained 592 mg. (45%) of the pure (S)(R)-diastereomer (m.p. 227°–229° C.) and 637 mg. (49%) of the pure (R)(R)-diastereomer (m.p. 222°–225° C.), as well as 267 mg. of mixed isomers.

The pure (S)(R)-diastereomer, viz., (4S)-6-fluoro-2,3-dihydro-3'-[(R)-1-phenylethylcarbamoyl]spiro[4H-1-benzopyran-4,4'-imidazolidine]-2',5'-dione, m.p. 227°–229° C., was further characterized by means of nuclear magnetic resonance data and elemental analysis: $^1$HNMR (300 MHz, DMSO-$d_6$)$\delta$1.40 (d, 3H), 2.26 (d, 1H), 2.75 (m, 1H), 4.30 (m, 1H), 4.45 (t, 1H), 4.77 (t, 1H), 6.85 (m, 1H), 7.03 (m, 1H), 7.11 (dd, 1H), 7.2–7.4 (m, 5H), 8.40 (d, 1H).

Anal. Calcd. for $C_{20}H_{18}FN_3O_4$: C, 62.66; H, 4.73; N, 10.93.

Found: C, 62.69; H, 4.63; N, 10.54.

The pure (R)-(R)-diastereomer, viz., (4R)-6-fluoro-2,3-dihydro-3'-[(R)-1-phenylethylcarbamoyl]spiro[4H-1-benzopyran-4,4'-imidazolidine]-2',5'-dione, m.p. 222°–225° C., was also further characterized by means of nuclear magnetic resonance data and elemental analysis: $^1$HNMR (300 MHz, DMSO-$d_6$)$\delta$1.40 (d, 3H), 2.28 (d, 1H), 2.86 (t, 1H), 4.32 (m, 1H), 4.47 (t, 1H), 4.76 (t, 1H), 6.80 (m, 1H), 6.95 (t, 1H), 7.06 (dd, 1H), 7.12–7.45 (m, 5H), 8.36 (d, 1H).

Anal. Calcd. for $C_{20}H_{18}FN_3O_4$: C, 62.66; H, 4.73; N, 10.93.

Found: C, 62.80; H, 4.43; N, 10.91.

EXAMPLE 2

The procedure described in Example 1 is repeated except that (S)-(−)-α-methylbenzyl isocyanate (Aldrich) is the reagent of choice employed in place of (R)-(+)-α-methylbenzyl isocyanate, using the same molar proportions as before. In this particular case, the corresponding (S)(S)- and (R)(S)-diastereomers are obtained, viz., (4S)-6-fluoro-3'-[(S)-1-phenylethylcarbamoyl]spiro[4H-1-benzopyran-4,4'-imidazolidine]-2',5'-dione and (4R)-6-fluoro-3'-[(S)-1-phenylethylcarbamoyl]spiro[4H-1-benzopyran-4,4'-imidazolidine-2',5'-dione, respectively.

In like manner, the use of (R)-(−)-1-(α-naphthyl)ethyl isocyanate (Aldrich) as reagent affords (4S)-6-fluoro-3'-[(R)-1-(α-naphthyl)ethylcarbamoyl]spiro[4H-1-benzopyran-4,4'-imidazolidine]-2',5'-dione and (4R)-6-fluoro-3'-[(R)-1-(α-naphthyl)ethylcarbamoyl]-spiro[4H-1-benzopyran-4,4'-imidazolidine]-2',5-dione, respectively, while the use of (S)-(+)-1-(α-naphthyl)ethyl isocyanate (Aldrich) as reagent affords (4S)-6-fluoro-3'-[(S)-1-(α-naphthyl)ethylcarbamoyl]spiro[4H-1-benzopyran-4,4'-imidazolidine]-2',5'-dione and (4R)-6-fluoro-3'-[(S)-1-(α-naphthyl)ethylcarbamoyl]-spiro[4H-1-benzopyran-4,4'-imidazolidine]-2',5'-dione, respectively.

EXAMPLE 3

Under a dry nitrogen atmosphere, in a flame-dried reaction flask, 820 mg. (0.02 mole) of 60% sodium hydride (dispersed in mineral oil) was washed with hexane to remove the oil and thereafter was suspended in 60 ml. of dry dimethylformamide with constant agitation. To the resulting stirred suspension, there were then added 5.13 g. (0.02 mole) of racemic 3'-chloro-5',6',7',8'-tetrahydro-spiro[imidazolidine-4,5'-quinoline]-2,5-dione (the product of Preparation E). The resulting white suspension was next stirred at room temperature (ca. 20° C.) for a period of 30 minutes, followed by the addition thereto of 3.0 g. (0.02 mole) of (R)-(+)-α-methylbenzyl isocyanate (Aldrich Chemical Co , Inc. of Milwaukee, Wisc.). The resulting reaction mixture was then stirred at room temperature for period of 18 hours, at which time thin layer chromatography (TLC) analysis (using ethyl acetate/hexane 1:1 by volume as the eluant) showed only the pair of diastereomers. Upon completion of this step, the reaction mixture was poured over 300 ml. of ice/water, then stirred and acidified to pH 4 with 1N hydrochloric acid, and the precipitated solids filtered and subsequently washed with water and air-dried to constant weight. The yield of diastereomeric product so obtained amounted to 8.03 g. (98%) and proved to be a mixture of diastereomeric ureides consisting of (5'R)- and (5'S)-3'-chloro-5',6',7',8'-tetrahydro-3-[(R)-1-phenylethylcarbamoyl]spiro[imidazolidine-4,5'-quinoline]-2,5-dione, melting at 140°-160° C. The latter mixture was then chromatographed by first dissolving 6.6 g. of said product in a minimal amount of ethyl acetate and adding the solution to a column of silica gel (230–400 mesh), using ethyl acetate/hexane (1:3 by volume) as the eluant. In this way, there were ultimately obtained 1.84 g. (56%) of the pure (S)(R)-diastereomer (m.p. 95°-100° C.), 1.50 g. (45%) of the pure (R)(R)-diastereomer (m.p. 80°-100° C.) and 2.04 g. of mixed isomers.

The pure (S)(R)-diastereomer, viz., (5'S)-3'-chloro-5',6',7',8'-tetrahydro-3-[(R)-1-phenylethylcarbamoyl]-spiro[imidazolidine-4,5'-quinoline]-2,5-dione (as the hemi-hexanate), m.p. 95°-100° C., was further characterized by means of nuclear magnetic resonance data and elemental analysis: $^1$HNMR (300 MHz, DMSO$_6$-d$_6$)δ 1.42 (d, 3H), 1.95 (bs, 1H), 2.22 (m, 2H), 2.50 (m, 2H), 2.85 (m, 2H), 4.80 (m, 1H), 7.10–7.36 (m, 5H), 7.95 (s, 1H), 8.36 (d, 1H), 8.41 (s, 1H).

Anal. Calcd. for $C_{20}H_{19}ClN_4O_3 \cdot 0.5 C_6H_{14}$ (hexane: C, 62.51; H, 5.93; N, 12.28. Found: C, 62.27; H, 5.68; N, 12.41.

The pure (R)(R)-diastereomer, viz., (5'R)-3'-chloro-5',6',7',8'-tetrahydro-3-[(R)-1-phenylethylcarbamoyl]-spiro-[imidazolidine-4,5'-quinoline]-2,5-dione (as the hemi-hexanate), m.p. 80°-100° C., was also further characterized by means of elemental analysis.

Anal. Calcd. for $C_{20}H_{19}ClN_4O_3 \cdot 0.5 C_6H_{14}$ (hexane): C, 62.51; H, 5.93; N, 12.28. Found: C, 62.67; H, 5.49; N, 12.26.

EXAMPLE 4

The procedure described in Example 3 is repeated except that (S)-(−)-α-methylbenzyl isocyanate (Aldrich) is the reagent employed in place of (R)-(+)-α-methylbenzyl isocyanate, using the same molar proportions as before. In this particular case, the corresponding (S)(S)- and (R)(S)-diastereomers are obtained, viz., (5'S)-3'-chloro-5',6',7',8'-tetrahydro-3-[(S)-1-phenylethylcarbamoyl]spiro[imidazolidine-4,5'-quinoline]-2,5-dione and (5'R)-3'-chloro-5',6',7',8'-tetrahydro-3-[(S)-1-phenylethylcarbamoyl]spiro[imidazolidine-4,5'-quinoline]-2,5-dione, respectively.

In like manner, the use of (R)-(−)-1-(α-naphthyl)ethyl isocyanate (Aldrich) as reagent affords (5'S)-3'-chloro-5',6',7',8'-tetrahydro-3-[(R)-1-(α-naphthyl)ethylcarbamoyl]spiro[imidazolidine-4,5'-quinoline]-2,5-dione and (5'R)-3'-chloro-5',6',7',8'-tetrahydro-3-[(R)-1-(α-naphthylethylcarbamoyl]spiro[imidazolidine-4,5'-quinoline]2,5-dione, respectively, while the use of (S)-(+)-1-(α-naphthyl)ethyl isocyanate (Aldrich) as reagent affords (5'S)-3'-chloro-5',6',7',8'-tetrahydro-3-[(S)-1-(α-naphthyl)ethylcarbamoyl]spiro[imidazolidine-4,5'-quinoline]-2,5-dione and (5'R)-3'-chloro-5',6',7',8'-tetrahydro-3-[(S)-1-(α-naphthyl)ethylcarbamoyl]-spiro[imidazolidine-4,5'-quinoline]-2,5-dione, respectively.

EXAMPLE 5

Under a dry nitrogen atmosphere, a mixture consisting of 200 mg. (0.00054 mole) of diastereomerically pure (4S)-6-fluoro-2,3-dihydro-3'-[(R)-1-phenylethylcarbamoyl]spiro[4H-1-benzopyran-4,4'-imidazolidine]-2',5'-dione[the(S)(R)-diastereomer product of Example 1] and 1.0 g. (0.0185 mole) of sodium methoxide (Fisher Scientific Co. of Fairlawn, N.J.) in 10 ml. of dry tetrahydrofuran was refluxed for a period of four hours and then allowed to cool to room temperature (ca. 20° C.), followed by a period of evaporation to near dryness while under reduced pressure. The residue thus obtained was then treated with 1N hydrochloric acid in sufficient amount to adjust the pH of the final solution to a value of ca. pH 7.5. The resulting solids were subsequently collected by means of suction filtration and air dried to constant weight to give a 392 mg. yield of solid product. The latter material was then chromatographed on silica gel, using ethyl acetate/hexane (1:1 by volume) as the mobile phase and there was eventually obtained 104 mg. (81%) of pure (4S)-(+)-6-fluoro-2,3-dihydro-spiro[4H-1-benzopyran-4,4'-imidazolidine]-2',5'-dione (sorbinil) in the form of white crystals melting at 237°-240° C.; $[\alpha]_D^{25°} + 54.8°$ (C=1 in methanol); $^1$HNMR (300 MHz, DMSO-d$_6$)δ2.15 (m, 1H), 2.30 (m, 1H), 4.20 (m, 1H), 4.50 (m, 1H), 6.90 (m, 2H), 7.10 (m, 1H), 8.60 (s, 1H). This product was substantially identical in every respect with the corresponding final product first reported as d-6-fluoro-spiro-[chroman-4,4'-imidazolidine]-2,',5'-dione [m.p. 241°-243° C.; $[\alpha]_D^{25°} + 54.0°$ (c=1 in methanol)] by R. Sarges in Example I of U.S. Pat. No. 4,130,174.

In like manner, when pure (4R)-6-fluoro-2,3dihydro-3'-[(R)-1-phenylethylcarbamoyl]spiro[4H-1-benzopyran-4,4'-imidazolidine]-2',5'-dione [the (R) (R)-diastereomer product of Example 1] and sodium methoxide were reacted together in accordance with this same procedure (using the same molar proportions as before), there was eventually obtained (after work-up) a 36% yield of pure (4R)-(−)-6-fluoro-2,3-dihydro-spiro-[4H-1-benzopyran-4,4'-imidazolidine]2',5'-dione in the form of a white crystalline solid melting at 235°-237° C.; $[\alpha]_D^{25°} - 54.1°$ (c=1 in methanol). This product was also substantially identical in every respect with the corresponding final product first reported as 1-6-fluoro-spiro-[chroman-4,4'-imidazolidine]-2',5'-dione m.p. 241°-243° C.; $[\alpha]_D^{25°} - 54.8°$ (c=1 in methanol)] by R. Sarges in Example I of U.S. Pat. No. 4,130,174.

EXAMPLE 6

The procedure described in Example 5 is repeated except that (4S)-6-fluoro-2,3-dihydro-3'-[(S)-1phenylethylcarbamoyl]spiro[4H-1-benzopyran-4,4'-imidazolidine [the first (S)(S)-diastereomer product of Example 2] is the starting material employed in lieu of the corresponding (S)(R)-diastereomer, using the same molar proportions as before, and (4S)-(+)-6-fluoro-2,3-dihydro-spiro-[4H-1-benzopyran-4,4'-imidazolidine]-2',5'-dione (sorbinil) is again the final product obtained.

In like manner, (4S)-6-fluoro-2,3-dihydro-3'-[(R)-1-(α-naphthyl)ethylcarbamoyl]spiro[4H-1-benzopyran-4,4'-imidazolidine]-2',5'-dione the (S)(R)-diastereomer product of Example 2] and (4S)-6-fluoro-2,3-dihydro-3'-[(S)-1-(α-naphthyl)ethylcarbamoyl]-spiro[4H-1-benzopyran-4,4'-imidazolidine]-2',5'-dione the second (S)(S)-diastereomer product of Example 2] also each afford sorbinil when respectively employed as starting materials in this very same reaction procedure.

EXAMPLE 7

Under a dry nitrogen atmosphere, in a dry reaction flask, a mixture consisting of 1.73 g. (0.00434 mole) of diastereomerically pure (5'S)-3'-chloro-5',6',7',8'-tetrahydro-3-[(R)-1-phenylethylcarbamoyl]-spiro[imidazolidine-4,5'-quinoline]-2,5-dione hemi-hexanate (the [(S)(R)-diastereomer product of Example 3] and 4.68 g. (0.086 mole) of sodium methoxide in 50 ml. of dry tetrahydrofuran was refluxed for a period of 18 hours, at which time thin layer chromatography (TLC) analysis (using ethyl acetate/hexane 1:1 by volume) showed only a small amount of unreacted starting material as being present. At this point, an additional 2.4 g. amount of sodium methoxide (0.044 mole) was added and refluxing was continued for a further period of 18 hours. Thin layer chromatography (TLC) analysis then showed only the desired hydantoin final product. Upon completion of this step, the reaction mixture (suspension) was cooled to room temperature (ca. 20° C.), concentrated in vacuo and then diluted with 100 ml. of water. The resulting aqueous solution was then acidified to pH 5.0 with 1N hydrochloric acid, and the white solid product so obtained was subsequently collected by means of suction filtration, washed with water and air dried to constant weight. Recrystallization of the latter material from methanol/chloroform then gave 848 mg. (78%) of pure (5'S)-3'-chloro-5',6',7',8'-tetrahydrospiro[imidazolidine-4,5'-quinoline]-2,5-dione in the form of fine white needles melting at 256°–258° C.; $[\alpha]_D^{25}$ +42.75° (c=1 in methanol); $^1$HNMR (300 MHz, DMSO-d$_6$)δ 1.92 (m, 2H); 2.15 (m, 2H), 2.90 (t, 2H), 7.62 (s, 1H), 8.50 (s, 1H), 8.57 (s, 1H).

Anal. Calcd. for $C_{11}H_{10}ClN_3O_2$: C, 52.50; H, 4.01; N, 16.70.

Found: C, 52.71; H, 4.23; N, 16.51.

In like manner, when 1.5 g. (0.00375 mole) of pure (5'R)-3'-chloro-5',6',7',8'-tetrahydro-3-[(R)-1-phenylethylcarbamoyl]spiro[imidazolidine-4,5'-quinoline]-2,5-dione hemi-hexanate (the (R)(R)-diastereomer product of Example 3) and 5.94 g. (0.110 mole) of sodium methoxide (thirty equivalents) in 50.ml. of dry tetrahydrofuran were refluxed together for a period of 18 hours in accordance with same procedure, there was eventually obtained (after work-up and recrystallization from methanol/chloroform) 890 mg. (94%) of pure (5'R)-3'-chloro-5',6',7',8'-tetrahydro-spiro[imidazolidine-4,5'-quinoline]-2,5-dione in the form of white needles melting at 258°–259° C., $[\alpha]_D^{25}$ −42.1° (c=1 in methanol).

Anal. Calcd. for $C_{11}H_{10}ClN_3O_2$: C, 52.50; H, 4.01; N, 16.70. Found: C, 52.71; H, 3.80; N, 16.43.

EXAMPLE 8

The procedure employed in Example 7 is repeated except that (5'S)-3'-chloro-5',6',7',8'-tetrahydro-3-[(S)-1-phenylethylcarbamoyl]spiro [imidazolidine-4,5'-quinolone]-2,5-dione the first (S)(S)-diastereomer product of Example 4] is the starting material employed in lieu of the corresponding (S)(R)-diastereomer, using the same molar proportions as before, and (5'S)-3'-chloro-5',6',7',8'-tetrahydro-spiro[imidazolidine-4,5'-quinoline]-2,5-dione is again the final product obtained.

In like manner, (5'S)-3'-chloro-5',6',7',8'-tetrahydro-3-[(R)-1-(α-naphthyl) ethylcarbamoyl]spiro[imidazolidine-4,5'-quinoline]-2,5-dione [the (S)(R)-diastereomer product of Example 4] and (5'S)-1-3'-chloro-5',6',7',8'-tetrahydro-3-[(S)-1-(α-naphthyl)ethylcarbamoyl]-spiro[imidazolidine-4,5'-quinoline]-2,5-dione [the second (S)(S)-diastereomer product of Example 4] also each afford (5'S)-3'-chloro-5',6',7',8'-tetrahydrospiro[imidazolidine-4,5'-quinoline]-2,5-dione when respectively employed as starting materials in this very same reaction procedure.

We claim:

1. A diastereomeric ureido compound of the formula

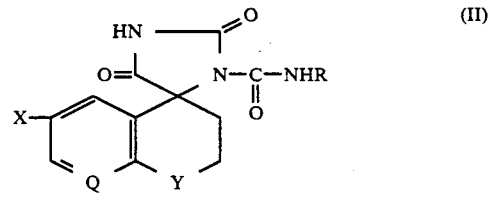

wherein:

X is hydrogen, fluorine, chlorine, bromine, $C_1$–$C_4$ alkyl or $C_1$–$C_4$ alkoxy;

Q is methine or nitrogen;

Y is methylene, oxygen or sulfur; and

R is (S)- or (R)-1-phenylethyl or (S)- or (R)-1-(1-naphthyl)ethyl.

2. A compound as claimed in claim 1 wherein X is fluorine, Q is methine, Y is oxygen and R is (R)-1-phenylethyl.

3. A compound as claimed in claim 1 wherein X is chlorine, Q is nitrogen, Y is methylene and R is (R)-1-phenylethyl.

4. (4S)-6-Fluoro-2,3-dihydro-3'-[(R)-1-phenylethylcarbamoyl]spiro-[4H-1-benzopyran-4,4'-imidazolidine]-2',5'-dione.

5. (5'S)-3'-Chloro-5',6',7',8'-tetrahydro-3-[(R)-1-phenylethylcarbamoyl]spiro[imidazolidine-4,5'-quinoline]-2,5-dione.

* * * * *